United States Patent [19]

Konoshima

[11] 4,433,675

[45] Feb. 28, 1984

[54] LIGHT SUPPLY APPARATUS FOR ENDOSCOPE

[75] Inventor: Katunaga Konoshima, Tokyo, Japan

[73] Assignee: Olympus Optical Co. Ltd., Tokyo, Japan

[21] Appl. No.: 361,885

[22] Filed: Mar. 25, 1982

[30] Foreign Application Priority Data

Apr. 1, 1981 [JP] Japan .................................. 56-49183

[51] Int. Cl.³ .............................................. A61B 1/06
[52] U.S. Cl. ........................................... 128/6; 362/32
[58] Field of Search ........................ 128/4, 6, 23, 721; 362/32, 295, 800; 200/DIG. 36

[56] References Cited

U.S. PATENT DOCUMENTS 3,081,765  3/1963  Kompelien ........................... 128/721
4,329,625  5/1982  Nishizawa et al. .................. 362/800
4,356,534 10/1982  Hattori ................................. 362/32

FOREIGN PATENT DOCUMENTS 2724939 12/1978 Fed. Rep. of Germany ... 200/DIG. 36

Primary Examiner—Edward M. Coven
Assistant Examiner—Max F. Hindenburg

[57] ABSTRACT

A light supply apparatus for endoscope, which comprises a lamp provided inside a housing for emitting light, a socket mounted on the housing, a connector of the endoscope being detachably connected to the socket, a detecting section including a LED and a photo-transistor which is provided within the socket so as to face each other and which optically detects the state of coupling between the connector and socket, and a light transmission restricting section for cutting off current supplied to the lamp when the connector is disconnected from the socket.

12 Claims, 5 Drawing Figures

F I G. 2
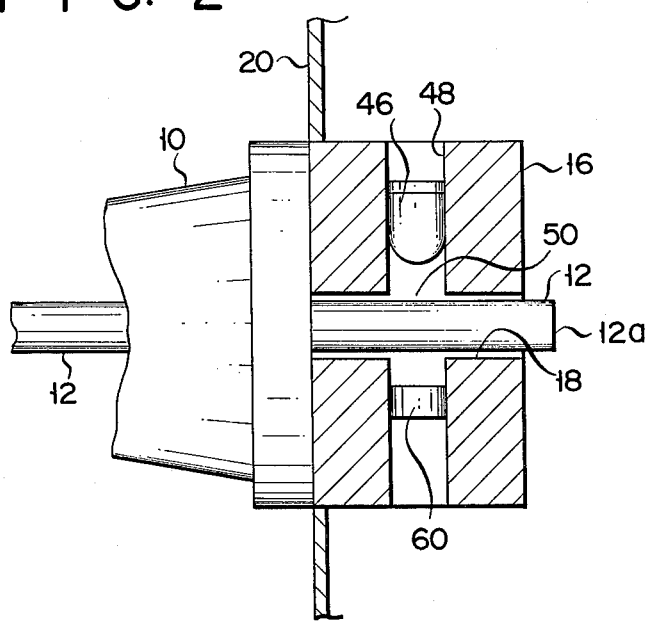
F I G. 3
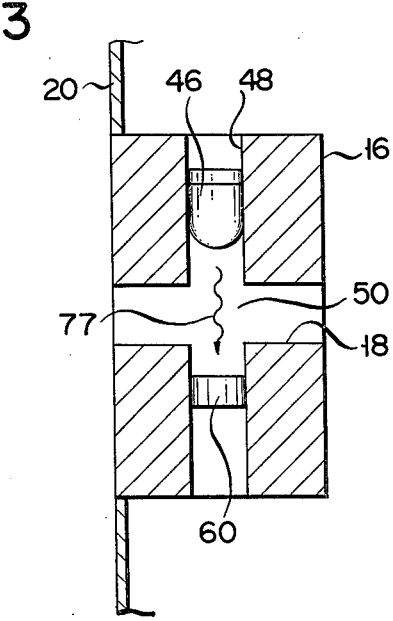

LIGHT SUPPLY APPARATUS FOR ENDOSCOPE

BACKGROUND OF THE INVENTION

The present invention relates to an illumination light supply apparatus for endoscope.

In the usual endoscope system, a connector which is coupled to the end of an universal cord, in which a light guide formed of an optical fiber or the like is inserted, is removably connected to a socket of a light supply apparatus. When the connector is connected to the socket, light from a light source is incident on the end surface of the light guide penetrating and projecting from an opening of the socket. The incident light is transmitted through the light guide to the endoscope to illuminate an object such as the surface of a cavity inside the human body.

The light source mentioned above generally includes a high brightness lamp which cannot recover to the "on" state right after it is turned off. The high brightness lamp accommodated in the light supply apparatus is, therefore, normally held "on" during the use of the light supply apparatus. When the connector is disconnected from the socket while the lamp is "on", however, the light from the lamp leaks to the outside of the light supply apparatus through the aforementioned opening. When this kind of light beam reaches the eyes, of the doctor or patient, he or she is dazzled by the light beam. Besides, this light beam is prone to the danger of radioactive radiation or like adverse effects.

U.S. patent application Ser. No. 195,440 discloses a light supply apparatus which can solve the above problems. With the light supply apparatus, when the light supply apparatus is disconnected from the socket, the quantity of light emitted from the light source and reaching a socket opening is automatically reduced to a predetermined level to solve the above-mentioned problems to a certain extent. However, with the apparatus, the state of coupling between the connector and socket is detected as a change of the state of a mechanical switch member such as a contact switch, becoming either on or off. The mechanical switch member has a voltage-bearing bare metal pin which is exposed at the outer surface of the socket from which the connector is disconnected. Therefore, the operator is prone to the hazard of electric shock in case if the operator occasionally touches the exposed metal pin. Further, depending upon the environmental conditions, the exposed portion of the metal pin is liable to be corroded by oxidization and covered by an undesired oxide film. In such a case, a contact failure of the contact switch member is occurred, whereby detection of the state of coupling between the connector and socket can no longer be done.

SUMMARY OF THE INVENTION

An object of the present invention is to provide a light supply apparatus for endoscope, which can eliminate such inconvenience as dazzlement due to leakage of the light beam from the socket when the connector of the endoscope is disconnected from the socket as well as being safe to the operator and highly reliable.

The light supply apparatus for endoscope according to the present invention comprises a light source and a socket member. The light source is provided inside a housing of the light supply apparatus and energized from a power source for emitting light. The socket member is mounted on the housing. A connector member, coupled to a light guide member for transmitting light to the endoscope, is detachably connected to the socket member. The state of coupling between the connector member and socket member is optically detected. When the connector member is disconnected from the socket member, the quantity of light emitted from the light source and reaching an opening, which is provided in the socket member and through which the light guide member penetrates, is reduced or blocked. After the removal of the connector member from the socket member light leaking to the outside of the apparatus through the opening of the socket member is reduced or blocked.

BRIEF DESCRIPTION OF THE DRAWINGS

FIG. 2 is a fragmentary enlarged-scale view showing a socket section of the light supply apparatus when a connector of FIG. 1 is connected to a socket;

FIG. 3 is a fragmentary enlarged-scale view showing the socket section of the light supply apparatus when the connector of FIG. 1 is removed from the socket;

DETAILED DESCRIPTION OF THE PREFERRED EMBODIMENTS

Figure 1:
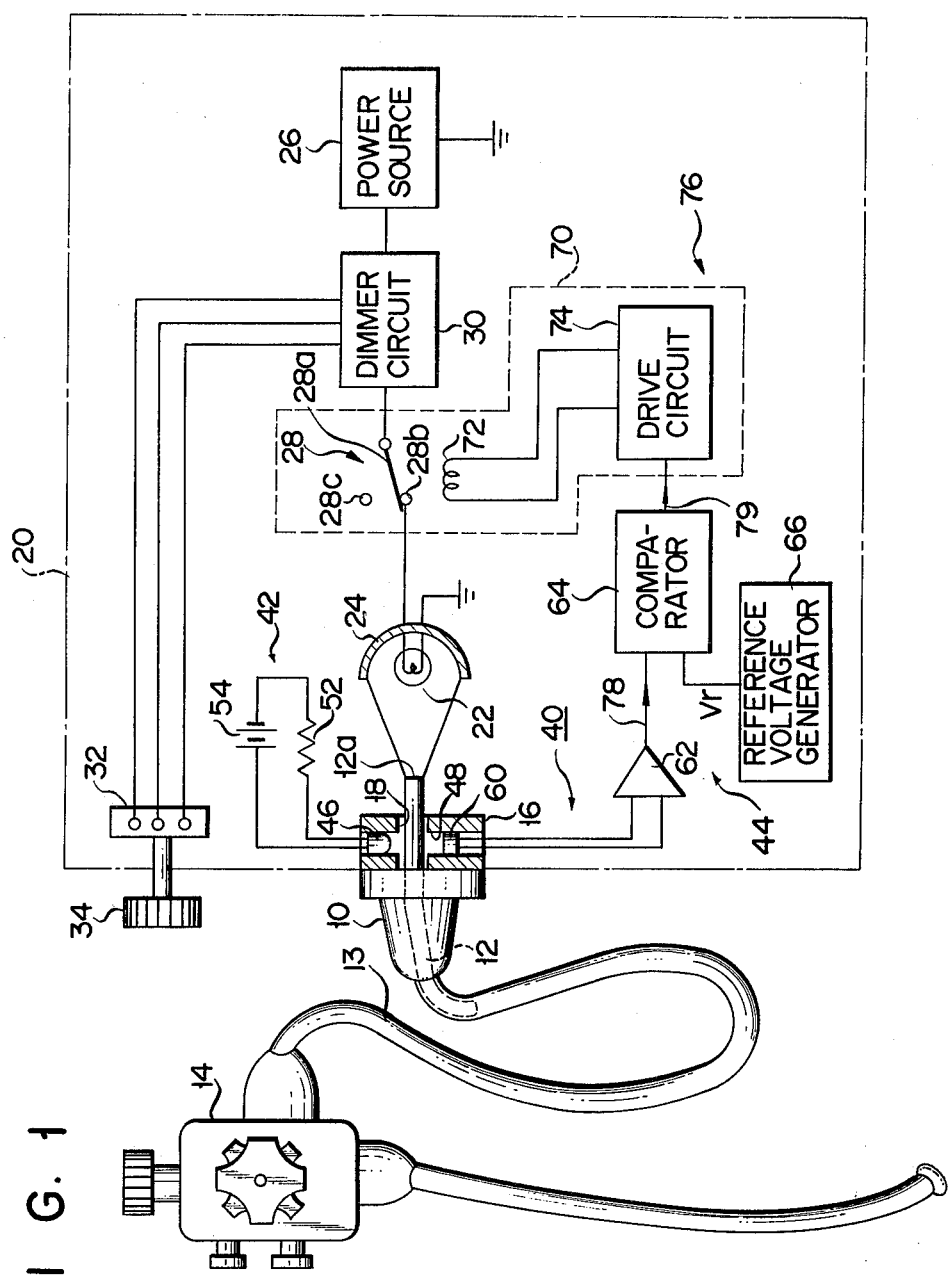
FIG. 1 is a block diagram illustrating an endoscope system including a light supply apparatus according to one embodiment of the present invention.

Referring now to FIG. 1, there is illustrated an endoscope system including one embodiment of the light supply apparatus for endoscope according to the present invention. To a connector 10 is connected a universal cord 13 accommodating a well-known light guide 12 for transmitting light for examination. The opposite end of the universal cord 13 is connected to an operating section of an endoscope 14. The connector 10 is arranged so as to detachably connected to a socket 16 provided at the front of a housing 20 of the light supply apparatus. When the connector 10 is attached to the socket 16, the light guide 12 accommodated in the connector 10 projects through an opening 18 in the socket 16 into the interior of the light supply apparatus. In this state, the distal end 12a of the light guide faces a light source lamp 22 provided within the housing 20. Light emitted from the lamp 22 is thus concentrated by a bowl-shaped mirror 24 onto the distal end 12a of the light guide 12. The light is transmitted, through the light guide 12 extending through the universal cord 13, to the endoscope 14.

Inside the housing 20, the lamp 22 is connected to a power source 26 through a relay switch 28 and a well-known dimmer circuit 30. The dimmer circuit 30 is connected to a well-known variable resistor 32 having a control knob 34. The dose of light emitted from the lamp 22 is continuously adjusted by operating the knob 34. Like the socket 16, the variable resistor 32 is secured to the housing 20.

A detecting section 40 which optically detects a connection and disconnection of the connector 10 to and from the socket 16 is provided within the housing 20. The detecting section 20 includes a light generating circuit 42 and a detection signal generating circuit 44. The light generating circuit 42 includes a lamp device which emits light for detection. For example, the lamp device includes a light-emitting device (LED) 46. The LED 46 is accommodated and secured in a passage 48 on one side of an opening 18, through which the light guide 12 extends in the socket 16 and which crosses the passage 48. The passage 48 of the socket 16 extends substantially at right angle to the opening 18 for the light guide, and the LED 46 is secured by a well-known method to the inner surface of the passage 48 in close contact therewith. The light from the LED 46, thus, illuminates an intersection region 50 between the passage 48 and opening 18. Returning to FIG. 1, the LED 46 is connected through a resistor 52 to a power supply 54 in a well-known manner.

The detection signal generating circuit 44 includes a light-detecting device 60, a signal amplifier 62, a comparator 64 and a reference voltage generating circuit 66. The light-detecting circuit 60 is formed of a light detector such as a photo-conductor, a photo-diode or a photo-transistor. As is shown in detail in FIG. 2, the light-detecting device 60 is accommodated in and secured to the passage 48 on the other side of the light guide 12. More particularly, the light detector 60 is held in close contact with the inner surface of the passage 48 such that it faces the LED 46 on the opposite side of the intersection region 50 between the opening 18 and passage 48. The output terminal of the light detector 60 is connected to an amplifier 62. When light from the LED 46 is received, the light detector 60 supplies the amplifier 62 with an electric signal corresponding to the light. The output terminal of the amplifier 62 is connected to a first input terminal of a comparator 64. A second input terminal of the comparator 64 is connected to the reference voltage circuit 66. The output terminal of the comparator 64 is connected to a light transmission restricting section 70.

The light transmission restricting section 70 includes, in addition to the relay switch 28, a solenoid 72 for switching the relay switch 28 and a drive circuit 74 connected to the solenoid 72. The comparator 64 is connected to the drive circuit 74. The drive circuit 74 is operated in response to the output signal of the comparator 64. The relay switch 28 is provided between the lamp 22 and dimmer circuit 30, and a movable contact 28a of the relay switch 28 is connected to a normally closed contact 28b of the lamp 22 in the normal state. When the solenoid 72 is excited by the drive circuit 74, the movable contact 28a of the relay switch 28 is switched to the side of a normally open contact 28c. The detecting section 40 and light transmission control section form a light control section 76.

Now, the operation of the endoscope system as one embodiment of the invention having the above construction will be described with reference to FIGS. 1 to 3. Now, the case when the connector 10 of the endoscope 14 is coupled to the socket 16 of the light supply apparatus will be described. At this time, light emitted from the LED 46 secured to the inside of the passage 48 of the socket 16 is blocked by the light guide 12 which is inserted in the opening 18. Thus, light from the LED 46 is not incident on the light detector 60 or is incident only in a very small quantity. Thus, the potential level of the signal supplied to the first input terminal of the comparator 64 is lower than the reference voltage Vr supplied from the reference voltage circuit 66. In this state, the drive circuit 74 is inoperative, and the solenoid 72 is not energized to hold the relay switch 28 in the closed state so that the light source 22 is powered by the power source 26 through the dimmer circuit 30. Thus, the light source 22 is "on" and supplies the illumination light for examination to the light guide 12.

When the connector 10 is disconnected from the socket 16, the light guide 12 is removed together with the connector 10 from the opening 18 of the socket 16. As shown in FIG. 3, light from the LED 46 is incident on the light detector 60 through the intersection region 50. At this time, the potential level of the detection signal 78 which is supplied through the amplifier 62 to the comparator 64 becomes higher than the reference voltage Vr. When the comparator 64, which compares the potential level of the detection signal 78 and the reference voltage Vr, judges that the former is higher than the latter, then it supplies the drive signal 79 to the drive circuit 74. In response to the signal 79, the drive circuit 74 energizes the solenoid 72, causing the movable contact 28a of the relay switch 28 to be switched to the side of the normally open contact 28c. As a result, the current path leading from the power source 26 to the light source 22 is disconnected so that the light source lamp 22 stops the light emission. As has been shown, as soon as the connector 10 is disconnected from the socket 16, the light source lamp 22 is caused to stop the light emission, thus there is no possibility of light leakage from the opening 18 of the socket 16. Further, with the embodiment of the invention, the state of coupling between the connector 10 and socket 16 is optically detected by the LED 46 and light detector 60 provided inside the socket 16. Therefore, there is no need of providing any bare voltage detection metal terminal outside the socket 16, and it is possible to enhance safety to the human body such as operator. Further, since the detecting section uses no metal part exposed to atmosphere, there is no possibility of reduction of the reliability of the detecting operation due to corrosion or the like.

Figure 4:
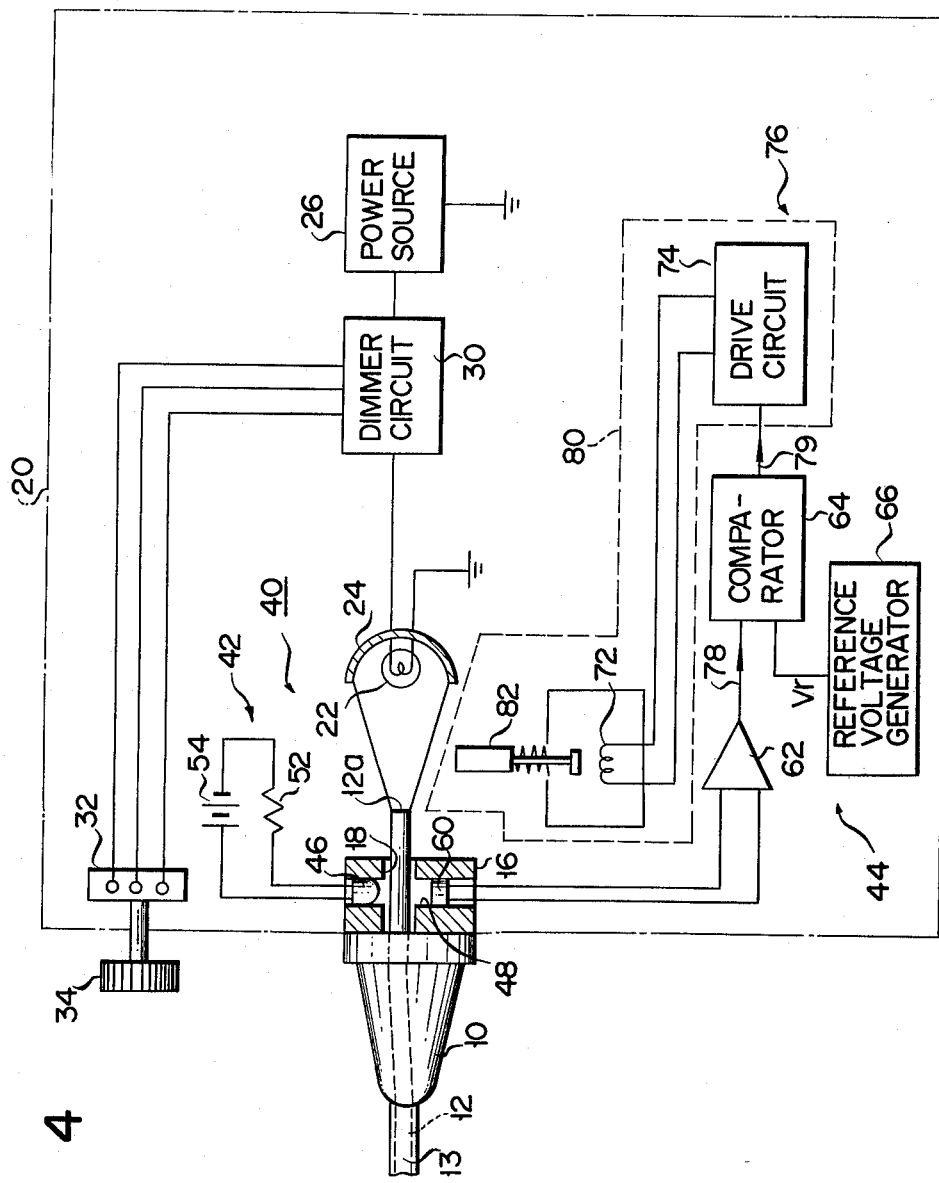
FIG. 4 is a block diagram showing a light supply apparatus according to another embodiment of the present invention.

FIG. 4 shows the internal construction of a different embodiment of the light supply apparatus according to this invention. The same parts as those in the preceding embodiment are designated by like reference symbols, and their description is omitted. Referring to FIG. 4, a light transmission restricting section 80, which is connected to detecting section 40 including light generating section 42 and signal generating section 44, includes a light shielding plate 82. Light control section 76 is constituted by the detecting section 40 and light transmission restricting section 80. The plate 82 is adapted to project into the light path between the lamp 22 and the distal end 12a of the light guide 12 when a solenoid 72 is energized. With this construction, when the removal of the connector 10 from the socket 16 is detected by the detecting section 40, the solenoid 72 is energized by the drive circuit 74. As a result, the light shielding plate 82 is projected into the light path between the lamp 22 and the distal end 12a of the light guide 12, and the light from the lamp 22 is thus prevented from being incident on the light guide 12 by the plate 82. Thus, it is possible to prevent leakage of light from the opening 18 of the socket 16 at the time of the removal of the connector 10 therefrom. In this embodiment, the light shielding plate 82 may be replaced with a light attenuation filter (not shown). As the light attenuation filter, a N.D. filter, a mesh filter (a metal mesh, for instance), etc. may be used. If the light attenuation filter is projected into the light path, a slight amount of component of the light from the light source lamp 22 is radiated to the outside through the socket opening 18. Thus, it is possible to overcome the dazzlement of the operator or like inconvenience also easily detect the breakage of a lead of the lamp 22 or like trouble.

Figure 5:
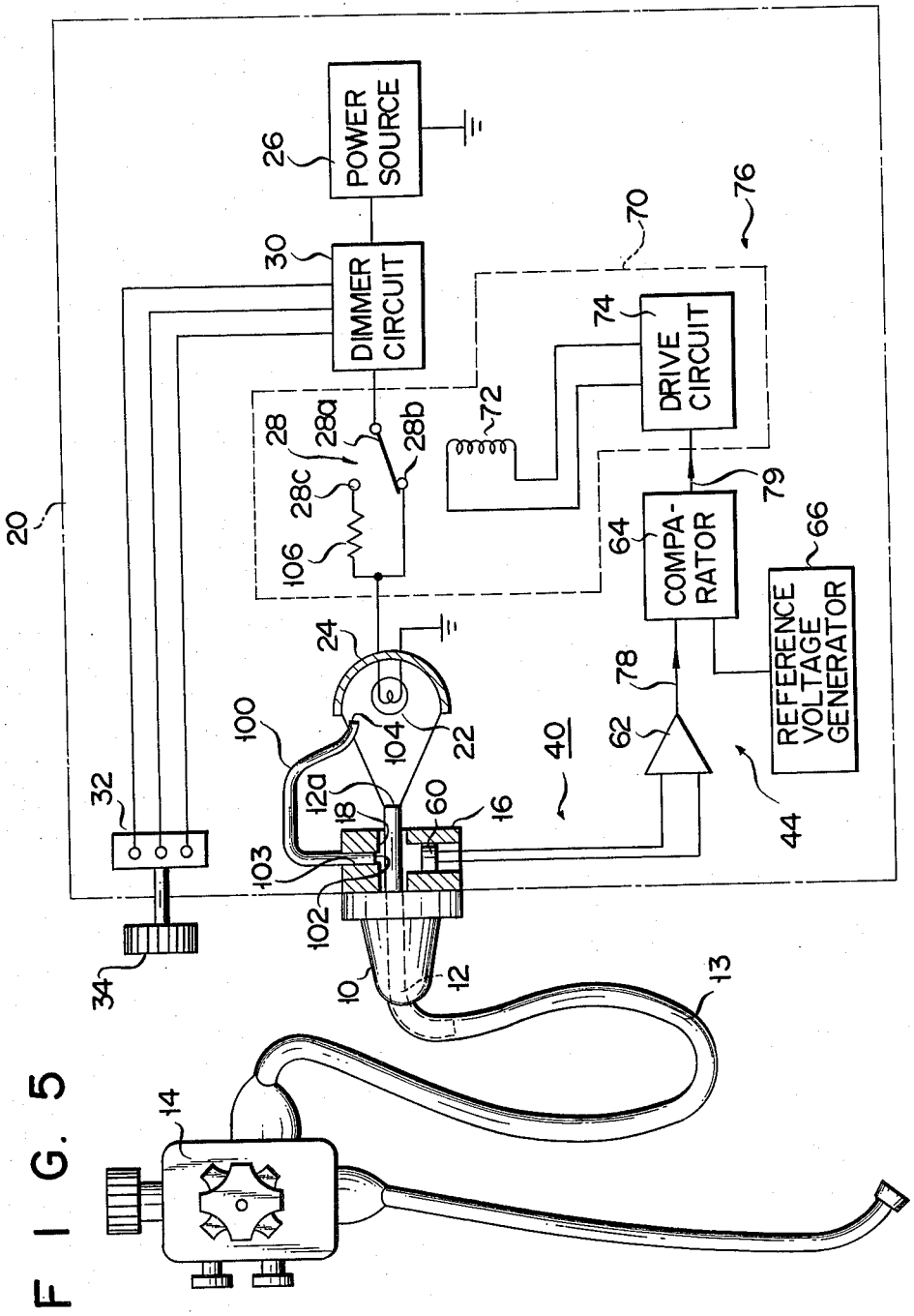
FIG. 5 is a block diagram illustrating an endoscope system including a light supply apparatus which is still another embodiment of this invention.

FIG. 5 shows an endoscope system incorporating a further embodiment of this invention. Referring to FIG. 5, a light guide 100 which serves to introduce light for detection is provided to extend into socket 16 and to face light detector 60. The light projection end 102 of the light guide 100 is inserted in and secured to a guide opening 103 which extends from one side of the socket 16 to light guide opening 18. The light incidence end 104 of the light guide 100 is secured, by a well-known method, at a position in the vicinity of the opening section of light collecting mirror 30. Thus, light emitted from the light source lamp 22 and reflected by the mirror 30 is partly introduced through the light guide 100 into the socket 16.

Normally open contact 28c of the relay switch 28, included in the light transmission restricting section 70, is connected through a resistor 106 to the light source lamp 22, while the normally closed contact 28b of the relay switch is directly connected to the lamp 22. Thus, current supplied to the lamp 22 can be changed to one of two values according to the switching operation of the relay switch 28. For the rest, the construction is the same as that of the preceding embodiments so that it will not be described any further.

In the embodiment of FIG. 5, when the connector 10 is connected to the socket 16, the light emitted from the distal end 102 of the light guide 100 is substantially blocked by the light guide 12 for the endoscope. As a result, light incident on the light detector 60 is greatly reduced, and the potential level of the electrical signal which is supplied to the comparator 64 becomes lower than the reference voltage Vr generated from the reference voltage circuit 66. Thus, the drive circuit 74 remains inoperative, and the movable contact 28a of the relay switch 28 is connected to the contact 28b. Current of the normal value is thus supplied to the lamp 22, causing the lamp 22 to emit light of the normal level. The subsequent operation is the same as described earlier in connection with the preceding embodiments, so it will not be described any further.

When the connector 10 is disconnected from the socket 16, light from the light guide 100 reaches the light detector 60 provided inside the socket 16. A signal having a higher potential level than the reference voltage Vr is supplied as the detection signal 78 to the comparator 64. The comparator 64 thus supplies the drive signal 79 to the drive circuit 74. The drive circuit 74 energizes the solenoid 72 in response to the signal 79. As a result, the movable contact 28a of the relay switch 28 is switched to the side of the contact 28c connected to the resistor 106. Thus, current from the power source 26 is caused to flow through the resistor 106, and the current value is thus reduced to a level which is determined by the resistance value of the resistor 106. In this way, the dose of leaking light from the opening 18 of the socket 16 after disconnecting the connector 10 is reduced.

With the embodiment of FIG. 5 which is constructed and operates in the manner as described above, the same effects as described earlier in connection with the previous embodiments can be obtained. In addition, since a light-emitting device such as an LED is unnecessary, the construction of the detecting section can be simplified. Further, the reduction of the light dose from the lamp 22 when the connector 10 is disconnected from the socket 16 is attained by a change in the current value supplied to the lamp 22. Therefore, it is possible to dispense with any mechanical movable member such as the light shielding plate 82 (FIG. 4) and thus improve the reliability.

Although the present invention has been shown and described with respect to particular embodiments, nevertheless, various changes and modifications which are obvious to a person skilled in the art to which the invention pertains are deemed to lie within the spirit, scope and contemplation of the invention.

What is claimed is:

1. An apparatus for supplying an illumination light to an endoscope which includes a light guide means for transmitting the light to the endoscope and a connector member coupled to the light guide means, said apparatus comprising:
    (a) a housing;
    (b) light source means, provided within said housing and connected to a power source section, for receiving electric power supplied from the power source section and for emitting light;
    (c) a socket member which is mounted on said housing and to which said connector member of said endoscope is detachably connected, said socket member having an opening through which said light guide means penetrates when said connector member is connected thereto; and
    (d) light control means for optically detecting a connection and disconnection of said connector member to and from said socket member, and for reducing an amount of light emitted from said light source means and transmitted to said opening of said socket member when said connector member is disconnected from said socket member, whereby the amount of light leaking to the outside of said housing through said opening is reduced, said light control means including,
        (i) detecting means for photoelectrically detecting the disconnection of said connector member from said socket member, said detecting means having light generating means for generating light of a predetermined light intensity, and signal generating means for receiving the light generated from said light generating means and for generating an output signal when the intensity of the light from said light generating means is changed to a level higher than a predetermined reference level, and
        (ii) light attenuation means, connected to said detecting means, for reducing the amount of light which is emitted from said light source means and which reaches said opening in response to said output signal.

2. An apparatus according to claim 1, wherein said light generating means includes a lamp device provided inside said socket member.

3. An apparatus according to claim 2, wherein said socket member has a passage penetrating said socket member and crossing said opening, said lamp device being provided within said passage and illuminating at least an intersection region between said opening and said passage.

4. An apparatus according to claim 3, wherein said lamp device is formed of a light-emitting diode.

5. An apparatus according to claim 2, wherein said signal generating means includes a light-detecting device which is provided within said socket so as to face said lamp member included in said light generating means and which receives the light from said lamp member and converts the received light into a corresponding electric signal.

6. An apparatus according to claim 3 or 5, wherein said light detecting device included in said signal generating means is provided within said passage of said socket member so as to face said lamp device via said intersection region.

7. An apparatus according to claim 6, wherein, when said connector member is connected to said socket member, said light guide means is inserted through said opening of said socket member, whereby the light from said lamp device is substantially blocked by said light guide means, and the amount of light reaching said light detecting device is reduced to a level lower than said predetermined level.

8. An apparatus according to claim 7, wherein said signal generating means further includes circuit means for receiving said electric signal outputted from said light-detecting device and for producing said output signal corresponding to said electric signal.

9. An apparatus according to claim 8, wherein said circuit means includes a comparator.

10. An apparatus according to claim 8, wherein said light-detecting device includes a light detector such as a photo-conductor, a photo-diode, a photo-transistor, etc.

11. An apparatus according to claim 1, wherein said light generating means includes light guide means having a light incidence end and a light projection end, said light incidence end of said light guide means being disposed in the vicinity of said light source means so as to receive part of said light emitted from said light source means.

12. An apparatus according to claim 3 or 11, wherein said light projection end of said light guide means is disposed within said passage of said socket member so as to face said lamp device via said intersection region.

* * * * *